United States Patent [19]

Sherman

[11] Patent Number: 6,132,772
[45] Date of Patent: *Oct. 17, 2000

[54] EXTENDED-RELEASE SOLID ORAL DOSAGE FORMS OF DRUGS HAVING LOW SOLUBILITY IN WATER

[76] Inventor: Bernard Charles Sherman, 50 Old Colony Road, Willowdale, Ontario, Canada, M2L 2K1

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,598

[22] PCT Filed: Jan. 19, 1996

[86] PCT No.: PCT/CA96/00056

§ 371 Date: Jul. 31, 1997

§ 102(e) Date: Jul. 31, 1997

[87] PCT Pub. No.: WO96/23499

PCT Pub. Date: Aug. 8, 1996

[30] Foreign Application Priority Data

Feb. 2, 1995 [NZ] New Zealand ............................ 270439

[51] Int. Cl.⁷ ...................................................... A61K 9/14
[52] U.S. Cl. .......................... 424/489; 424/461; 424/480; 424/468; 424/501
[58] Field of Search ..................................... 424/489, 480, 424/457, 461, 468, 501

[56] References Cited

U.S. PATENT DOCUMENTS

| | | | |
|---|---|---|---|
| 4,412,986 | 11/1983 | Kawata et al. | 424/480 |
| 4,673,564 | 6/1987 | Kawata et al. | |
| 4,765,989 | 8/1988 | Wong et al. | |
| 5,455,046 | 10/1995 | Baichwal | 424/457 |

FOREIGN PATENT DOCUMENTS

| | | |
|---|---|---|
| 0 557 244 | 8/1993 | European Pat. Off. . |
| 56-115726 | 9/1981 | Japan . |
| WO 94/23700 | 10/1994 | WIPO . |

OTHER PUBLICATIONS

Database WPI, Section Ch, Week 9602, Derwent Publications Ltd., London, Great Britain; Class A96,, AN 96–017127, XP002002077 & JP, A, 07 291 854 (Tanabe Seiyaku), Nov. 7, 1995.

*Primary Examiner*—Thurman K. Page
*Assistant Examiner*—William E. Benston, Jr.
*Attorney, Agent, or Firm*—Nixon & Vanderhye P.C.

[57] ABSTRACT

The present invention relates to extended-release solid oral dosage forms of a drug having low solubility in water are obtained by dissolving the drug in polyethylene glycol having a mean molecular weight of at least 1000 and adding thereto a hydrophilic gel-forming polymer.

12 Claims, No Drawings

EXTENDED-RELEASE SOLID ORAL DOSAGE FORMS OF DRUGS HAVING LOW SOLUBILITY IN WATER

FIELD OF INVENTION

The present invention is related to pharmaceutical extended release compositions for oral administration containing a drug having low solubility in aqueous media.

BACKGROUND

Pharmaceuticals with low solubility in water cause formulation problems due to their poor rate and extent of dissolution in aqueous media (including gastrointestinal fluids), which results in low absorption into systemic circulation after oral ingestion.

Examples of drugs with low solubility in water are some substituted dihydropyridine compounds, such as nifedipine, felodipine, ninodipine, isradipine, nitrendipine, nicardipine, niludipine, nisoldipine, and amlodipine. These compounds are classified as calcium antagonists, which are widely used for the treatment of cardiovascular disorders such as hypertension.

In order to make a composition containing such a drug that will enable maximum absorption from the gastrointestinal tract, it is necessary to incorporate in the composition a feature that increases the solubility of the drug to enable it to dissolve in the gastrointestinal fluids.

Several ways to increase the solubility have been described in prior literature. One way is described in U.S. Pat. No. 4,673,564, wherein nicardipine is used in its amorphous form in order to obtain increased dissolution and absorption. British patent 1456618 discloses improving the dissolution and absorption of nifedipine by preparation of a solid solution of nifedipine in polyethylene glycol in the presence of a surface active agent.

U.S. Pat. No. 4,412,986 discloses improving the dissolution and absorption of nifedipine by preparing a co-precipitate with a water-soluble polymer.

A feature that increases the solubility of a drug and thereby increases the extent of absorption will generally also increase the rate of absorption of the drug. If a drug is absorbed rapidly, and particularly if it is also eliminated rapidly, it becomes necessary to administer the drug frequently (i.e. several times per day) in order to maintain uniform blood levels. This is an undesirable situation, as frequent dosing is inconvenient for the patient and may lead to noncompliance by the patient.

To overcome this problem, it is necessary to include in the composition, in addition to a first feature to increase solubility of the drug, a second feature to slow down and control the rate at which the drug is released from the composition and made available for dissolution and absorption. A composition with such a feature is referred to in the trade as "extended release" or "controlled release".

The prior literature discloses numerous ways to make extended release compositions which slow-down and control the rate of dissolution and absorption of a drug. Such formulations usually include a substance such as a wax, fatty material, or polymer which causes the composition (usually in the form of a tablet) to erode or dissolve slowly in gastrointestinal fluids thereby slowly releasing the drug contained in the composition.

Especially preferred substances to slow-down the dissolution are hydrophillic gel-forming polymers (usually water-soluble cellulose derivatives). When a composition containing sufficient quantity of such a polymer is ingested and comes into contact with the gastrointestinal fluids, the hydrophillic gel-forming polymer nearest the surface of the composition hydrates to form a viscous gel layer around the surface of the solid mass. Because of the high viscosity, the viscous layer dissolves away only gradually, exposing the material below to the same process. The mass thus dissolves away only slowly, thereby slowly releasing the active ingredient into the gastrointestinal fluid.

In order to produce an extended release composition of a drug having very low solubility in water, it is necessary to have one feature as aforesaid to increase the solubility and a second feature as aforesaid to slow down and control the rate of dissolution.

The prior art also discloses numerous compositions which include a feature of each type to achieve extended release of a drug having low solubility in water.

European patent application 0557-244-A1 discloses compositions which contain nifedipine which has been micronized to small crystals to increase solubility, along with a hydrophillic gel-forming polymer to slow-down and control the rate of dissolution and absorption from the composition. A problem with the compositions disclosed in this patent is the smallest size to which nifedipine can be micronized using conventional equipment is about 1 micron, and this particle size is still not small enough to enable full dissolution and absorption of the nifedipine. Moreover, unless the crystal size is carefully controlled to be the same in every batch of tablets, release characteristics may vary from batch to batch.

U.S. Pat. No. 4,765,989 discloses extended release formulations of nifedipine in the form of an osmotic device, which is relatively difficult and expensive to manufacture.

Accordingly, it is the object of this invention to provide an extended release composition for oral administration of a drug having low solubility which can be manufactured by simple and inexpensive techniques, which does not require micronization of the drug.

It is a further object to provide an extended release composition for oral administration of a drug having low solubility for which the dissolution and absorption characteristics of the compositions are not affected by the crystal form or the particle size distribution of the drug used to make the composition.

DESCRIPTION OF THE INVENTION

One feature of the invention is that the drug is solubilized by dispersing it in polyethylene glycol having mean molecular weight of at least 1000. Such polyethylene glycols are solids at normal room temperatures.

Such polyethylene glycols are sold, for example, under the tradename Carbowax by Union Carbide Corporation. Carbowax 1000 has an average molecular weight of about 1000 and a melting point of about 38° C. Carbowax 1450 has an average molecular weight of about 1450 and a melting point of about 56° C. Carbowax 3350 has an average molecular weight of about 3350 and a melting point of about 56° C., and Carbowax 8000 has an average molecular weight of about 8000, and a melting point of about 61° C.

The drug is dispersed in the polyethylene glycol by heating the polyethylene glycol to a temperature above its melting point, adding the drug, blending the mixture so as to dissolve all or at least most of the drug in the molten polyethylene glycol, and cooling the mixture so that it is again solidified.

It will be thus understood that the compositions and processes of the within invention are applicable to drugs that have low solubility in water but are adequately soluble in polyethylene glycols to enable the drug to be dissolved in the molten polyethylene glycol.

For drugs having only moderate solubility in polyethylene glycols, the amount dissolved can be increased by blending at higher temperatures. For example, the drug nifedipine can be fully dissolved at concentrations as much as 1 gram of drug per gram of polyethylene glycol by blending at temperatures between 100° C. and 150° C.

As the molten mass cools and solidifies, the solution may become supersaturated. However, because of the high viscosity of the blend, the drug, once dissolved at elevated temperatures, will generally remain well dispersed in the resolidified material.

Because the drug is dissolved in the process as aforesaid, the properties of the composition are independent of the crystal form or particle size of the drug at the beginning of the process. Hence, any need to control the crystal form or particle size of the drug is eliminated.

The amount of polyethylene glycol used will usually be at least equal to the amount of the drug by weight. Preferably the amount of polyethylene glycol will be from 1.5 to 10 times the amount of the drug by weight, and most preferably from 2 to 5 times the amount of the drug by weight.

After the molten material has been cooled and has solidified, it is ground up into granules. The granules can then be mixed with other inactive ingredients and compressed into tablets.

Although polyethylene glycol having an average molecular weight as low as 1000 may be used, is as preferred to use polyethylene glycol with an average molecular weight of at least about 3350, because the higher melting point makes it easier to grind the resolidified product into granules.

Another feature of the invention is that, in addition to containing the drug dispersed in polyethylene glycol having a mean molecular weight of at least 1000, the composition also contains a hydrophillic gel-forming polymer, which serves to slow down and control the rate of dissolution in gastrointestinal fluids.

As explained previously, the result of including a suitable hydrophillic gel-forming polymer in sufficient quantity is that, when the composition is ingested and comes into contact with the gastrointestinal fluids, the hydrophillic gel-forming polymer nearest the surface hydrates to form a viscous gel layer around the surface of the solid mass. Because of the high viscosity, the viscous layer dissolves away only gradually, exposing the material below to the same process. The mass thus dissolves away only slowly, thereby slowly releasing the active ingredient into the gastrointestinal fluids.

Suitable hydrophillic gel-forming polymers include, but are not necessarily limited to, hydroxypropyl methylcellulose, hydroxypropyl cellulose, methylcellulose, sodium carboxymethylcellulose, hydroxyethylcellulose, and polyethylene oxide. For any given polymer type, use of a material with higher average molecular weight provides higher viscosity in aqueous solution of any given concentration; hence use of a higher molecular weight generally enables use of a lesser quantity of polymer to accomplish the required retardation of dissolution. The polymers used will usually but not necessarily be those that give a viscosity of more than 100 cps in 2 percent aqueous solution.

Preferred hydrophillic gel-forming polymers are selected from hydropropyl methylcellulose, hydroxypropyl cellulose and hydroxyethyl cellulose. Especially preferred is hydroxypropyl methylcellulose having 19–24% methoxyl substitution and 7–12% hydroxypropyl substitution, and having a number average molecular weight of at least 20,000.

Such polymers include those sold by Dow Chemical Co. under the tradenames Methocel K4M, Methocel K15M and Methocel K100M.

The hydrophillic gel-forming polymer may be incorporated into the composition in either of two ways.

One way is to blend either part or all of the hydrophillic gel-forming polymer, along with the drug, into the molten polyethylene glycol before it is solidified and ground into granules.

The other way is to add part or all of the hydrophillic gel-forming polymer by mixing it with the solid dispersion of the drug in polyethylene glycol after it is solidified and ground into granules.

It will also be understood that the dosage forms according to the invention may contain other ingredients in addition to the active drug, polyethylene glycol, and the hydrophillic gel-forming polymer.

For example, there may be included a lubricant necessary to avoid sticking of the material to the punches in the tabletting process. Suitable lubricants include but are not limited to stearic acid, magnesium stearate and other metal stearates.

Further it will be understood that, as is the case with the hydrophillic gel-forming polymer, the lubricant and other inactives may be incorporated by blending these into the molten polyethylene glycol along with the drug. Alternatively, the lubricant and other ingredients may be mixed with the solid dispersion of drug in polyethylene glycol after it is solidified and ground into granules.

Dosage forms according to the present invention may take the form of tablets, which may be produced by compressing the final mix of granules and/or powders into tablets on tablet press. The tablets may be uncoated or may have a film-coating applied to their surfaces using any of a number of polymer systems and processes well known in the art.

A film coating, if used, may be a coating that does not further delay release of the drug from the tablet, or it may be an insoluble but permeable coating that further retards dissolution.

A film coating having no delaying action may consist, for example, of a film-former, plasticizer, and pigments. The film-former may consist of a water-soluble polymer such as low-viscosity hydroxypropyl methylcellulose; for example Methocel E5 or E15 (brand names of Dow Chemicals Ltd.).

A film coating having delaying action may consist of water-insoluble but water-permeable polymers. Preferred water insoluble polymers are derivatives of methacrylic acid, such as Eudragit RS or RL or L (brand names of Rohm Pharma GmbH).

As aforesaid, the film coating may also contain excipients customary in film coating procedures, such as light-protecting pigments; for example iron oxides or titanium dioxide, and plasticizers.

Alternatively, dosage forms according to the present inventions may take the form of capsules, which may be made by filling empty capsule shells either with granules of the solid dispersion or with a mix of granules of solid dispersion and other ingredients.

Alternatively, dosage forms according to the present invention may take the form of capsules made by filling empty capsule shells with a dispersion of the drug and hydrophillic gel-forming polymer in molten polyethylene glycol when it is still in molten form and allowing it to cool and solidify after the capsules are filled.

The production of compositions within the scope of the invention will be further illustrated by the following examples, which are intended to be illustrative but not limiting of the scope of the invention.

EXAMPLE 1

Tablets were made using ingredients in the following proportions:

| | |
|---|---|
| Carbowax 8000 | 50. |
| nifedipine | 20. |
| stearic acid | 5. |
| Methocel K100M | 15. |
| | 90. |

The Carbowax 8000 was melted and further heated while stirring to a temperature of 120° C. The nifedipine was added and the mixture was stirred until the nifedipine was fully dissolved. The stearic acid was added and mixing was continued until the stearic acid melted and was dissolved in the mixture.

The methocel K100M was then added and mixing continued for several minutes. The mixture was then poured into trays and allowed to cool and solidify.

The solid was then removed from the trays and ground into granules. The granules were than made into tablets having a tablet weight of 90 mg each.

Each tablet thus contained 20 mg of nifedipine.

A film coating then was applied by spraying onto the tablets an aqueous solution containing Methocel E5 as polymer, Carbowax 3350 as plasticizer and iron oxide and titanium dioxide as pigments.

The rate of absorption of nifedipine from these tablets was determined in a study in which tablets were ingested by human volunteers, and blood samples were drawn and tested.

It was found that the time to peak blood levels for this formulation was about 3 hours, (versus under 1 hour for an immediate release composition), so that this formulation is suitable for twice daily administration.

EXAMPLE 2

Tablets were made using ingredients in the following proportions:

| | |
|---|---|
| Carbowax 8000 | 97. |
| nifedipine | 33. |
| Methocel K100M (Part 1) | 40. |
| magnesium stearate | 0.6 |
| colloidal silicon dioxide | 0.4 |
| Methocel K100M (Part 2) | 79. |
| | 250. |

The Carbowax 8000 was melted and further heated while stirring to a temperature of 120° C. The nifedipine was added and the mixture was stirred until the nifedipine was fully dissolved.

The Methocel K100M (part 1) was then added and mixing continued for several minutes. The mixture was then poured into trays and allowed to cool and solidify.

The solid was then removed from the trays and ground into granules.

The granules were placed into a mixer, along with the magnesium stearate, colloidal silicon dioxide and Methocel K100M (part 2) and all these ingredients were mixed together.

This mixture of granules and powders was then made into tablets having a weight of 250 mg each. Each tablet thus contained 33 mg of nifedipine.

A film coating was then applied to the tablets using Eudragit L as polymer, triethyl citrate as plasticizer and iron oxide and titanium dioxide as pigments.

The rate of absorption of nifedipine from these tablets was determined in a study in which tablets were ingested by human volunteers, and blood samples were drawn and tested. It was found that the time to peak blood levels for this formulation was about 12 hours, so that this formulation is suitable for one daily administration.

What I/We claim is:

1. An extended release solid pharmaceutical composition suitable for oral administration produced by a process comprising the steps of:

i) melting a polyethylene glycol having a mean molecular weight of at least 1000 so that said polyethylene glycol is in a molten state, ii) blending into said molten polyethylene glycol resulting from step (i) a drug having a solubility of less than 0.1% by weight in water at 20°, iii) cooling the molten blend resulting from step (ii) so as to render said blend a solid, and iv) grinding into granules said solid resulting from step (iii) and adding thereto a slow release agent in the form of a hydrophilic gel-forming polymer having a mean molecular weight of at least 20,000 so that said extended release solid pharmaceutical composition is formed.

2. An extended release solid pharmaceutical composition suitable for oral administration produced by a process comprising the steps of:

i) melting a polyethylene glycol having a mean molecular weight of at least 1000 so that said polyethylene glycol is in a molten state, ii) blending into said molten polyethylene glycol resulting from step (i) a drug having a solubility of less than 0.1% by weight in water at 20° and a slow release agent in the form of a hydrophilic gel-forming polymer having a mean molecular weight of at least 20,000, iii) cooling the molten blend resulting from step (ii) so as to render said blend a solid, and iv) grinding into granules said solid resulting from step (iii) so that said extended release solid pharmaceutical composition is formed.

3. A composition as in claim 2 wherein the drug is nifedipine.

4. A composition according to claim 1 or 2 wherein the ratio of the weight of the polyethylene glycol to the weight of drug is at least sufficient so that at the temperature at which the drug is blended into the polyethylene glycol, all or at least most of the drug dissolves in the polyethylene glycol.

5. A composition according to claim 1 or 2 wherein the hydrophillic gel-forming polymer is a cellulose derivative.

6. A composition according to claim 5 wherein the hydrophillic gel-forming polymer is a hydroxypropyl methylcellulose.

7. A composition according to claim 6 wherein the hydroxypropyl methylcellulose has a hydroxypropyl content of 4–12% by weight.

8. A composition according to claim 7 wherein the hydroxypropyl methylcellulose has a methoxyl content of 19–24% by weight and a hydroxypropyl content of 7–12% by weight.

9. A composition according to claim 1 or 2 in the form of a tablet.

10. A composition as in claim 1 wherein the drug is a substituted dihydropyridine.

11. A composition according to claim 1 wherein step (iv) further comprises adding, in addition to said slow release agent, magnesium stearate or colloidal silicon dioxide.

12. A composition according to claim 2 wherein step (iv) further comprises adding stearic acid or magnesium stearate.

* * * * *